(12) United States Patent
Rueeck et al.

(10) Patent No.: US 9,927,449 B2
(45) Date of Patent: Mar. 27, 2018

(54) METHOD OF USING CUVETTE PACKAGE WITH RFID PARAMETER TRANSPONDER AND CUVETTES WITH 2D BAR CODE, INCLUDING PHOTOMETRY

(75) Inventors: Gabriel Rueeck, Berlin (DE); Helga Guthmann, Grevenbroich (DE); Johannes Berssen, Panketal (DE); Michael Ziedrich, Berlin (DE); Carsten Schulz, Dormagen (DE); Clemens Hanschke, Berlin (DE); Florens Engel, Stahmsdorf (DE); Dietmar Zangenberg, Duesseldorf (DE); Markus Lenhard, Viersen (DE); Thomas Coeper, Duesseldorf (DE)

(73) Assignee: HACH LANCE GMBH, Berlin (DE)

( * ) Notice: Subject to any disclaimer, the term of this patent is extended or adjusted under 35 U.S.C. 154(b) by 1707 days.

(21) Appl. No.: 13/498,707

(22) PCT Filed: Oct. 1, 2009

(86) PCT No.: PCT/EP2009/062777
§ 371 (c)(1),
(2), (4) Date: Jun. 12, 2012

(87) PCT Pub. No.: WO2011/038769
PCT Pub. Date: Apr. 7, 2011

(65) Prior Publication Data
US 2012/0244628 A1    Sep. 27, 2012

(51) Int. Cl.
*G01N 35/00*     (2006.01)
*B01L 3/00*      (2006.01)
*B01L 9/06*      (2006.01)

(52) U.S. Cl.
CPC ...... *G01N 35/00732* (2013.01); *B01L 3/5453* (2013.01); *B01L 9/06* (2013.01); *B01L 2200/143* (2013.01); *B01L 2300/022* (2013.01)

(58) Field of Classification Search
CPC ...... G01N 30/24; G01N 30/38; G01N 35/025; G01N 21/6458; G01N 35/10;
(Continued)

(56) References Cited

U.S. PATENT DOCUMENTS

2005/0205673 A1    9/2005   Morris et al.
2009/0124015 A1*   5/2009   Dussi et al. .................. 436/43
(Continued)

FOREIGN PATENT DOCUMENTS

DE    41 09 118 A1    9/1992
EP    1 767 948 A2    3/2007
(Continued)

*Primary Examiner* — Yelena G Gakh
(74) *Attorney, Agent, or Firm* — Norman B. Thot

(57) ABSTRACT

A liquid analysis system for a photometric determination of an analyte in a liquid sample includes an analyzer comprising a photometer, an RFID parameter reading device and an identifier reading device, and a cuvette package comprising an RFID parameter transponder and a plurality of test cuvettes of one batch. Each test cuvette comprises a reagent. Batch identification and batch-specific reagent data are stored in the RFID parameter transponder. Each test cuvette comprises a batch-specific identifier including a batch identification. The batch identification is configured to be read by the identifier reading device.

2 Claims, 1 Drawing Sheet

(58) Field of Classification Search
CPC . G01N 2021/6417; G01N 2035/00326; G01N 2035/1062; G01N 21/64; G01N 21/6452; G01N 33/48771; G01N 35/00722; G01N 21/03
USPC .... 422/50, 401–405; 436/164–166, 171–172
See application file for complete search history.

(56) References Cited

U.S. PATENT DOCUMENTS

| | | |
|---|---|---|
| 2009/0130745 A1 | 5/2009 | Williams et al. |
| 2010/0025464 A1 | 2/2010 | Truceb et al. |
| 2010/0188244 A1 | 7/2010 | Sattler et al. |

FOREIGN PATENT DOCUMENTS

| | | |
|---|---|---|
| EP | 2 020 263 A1 | 2/2009 |
| EP | 2 080 553 A1 | 7/2009 |

* cited by examiner

METHOD OF USING CUVETTE PACKAGE WITH RFID PARAMETER TRANSPONDER AND CUVETTES WITH 2D BAR CODE, INCLUDING PHOTOMETRY

CROSS REFERENCE TO PRIOR APPLICATIONS

This application is a U.S. National Phase application under 35 U.S.C. § 371 of International Application No. PCT/EP2009/062777, filed on Oct. 1, 2009. The International Application was published in German on Apr. 7, 2011 as WO 2011/038769 A1 under PCT Article 21(2).

FIELD

The present invention provides a liquid analysis system for a photometric determination of an analyte in a liquid sample.

BACKGROUND

DE 41 09 118 C2 describes a system where the analysis system is formed by an analyzer and test cuvettes, with a plurality of test cuvettes of a batch, combined in a cuvette package, being transported to the user or to the analyzer. The test cuvettes are each provided with an identifier in the form of a one-dimensional bar code. The identifier contains information about the type of the cuvette test, i.e., about the analyte that can be determined using the cuvette test, or about the type of reagent present for that purpose in the test cuvette. The analyzer includes a memory with a database that stores reagent data types of cuvette tests and reagents, which date can be used for measurement and the evaluation of the measurement. Examples of reagent data are batch-specific correction factors, shelf life information etc., which each have to be input manually into the analyzer, since the storage capacity of the bar code is insufficient to hold this information.

A manual input of reagent data is error-prone and cumbersome.

SUMMARY

An aspect of the present invention is to provide a liquid analysis system that is easier to handle and less error-prone, as well as a method for operating such an analysis system.

In an embodiment, the present invention provides a liquid analysis system for a photometric determination of an analyte in a liquid sample which includes an analyzer comprising a photometer, an RFID parameter reading device and an identifier reading device, and a cuvette package comprising an RFID parameter transponder and a plurality of test cuvettes of one batch. Each test cuvette comprises a reagent. Batch identification and batch-specific reagent data are stored in the RFID parameter transponder. Each test cuvette comprises a batch-specific identifier including a batch identification. The batch identification is configured to be read by the identifier reading device.

BRIEF DESCRIPTION OF THE DRAWINGS

The present invention is described in greater detail below on the basis of embodiments and of the drawings in which.

DETAILED DESCRIPTION

Figure 1:
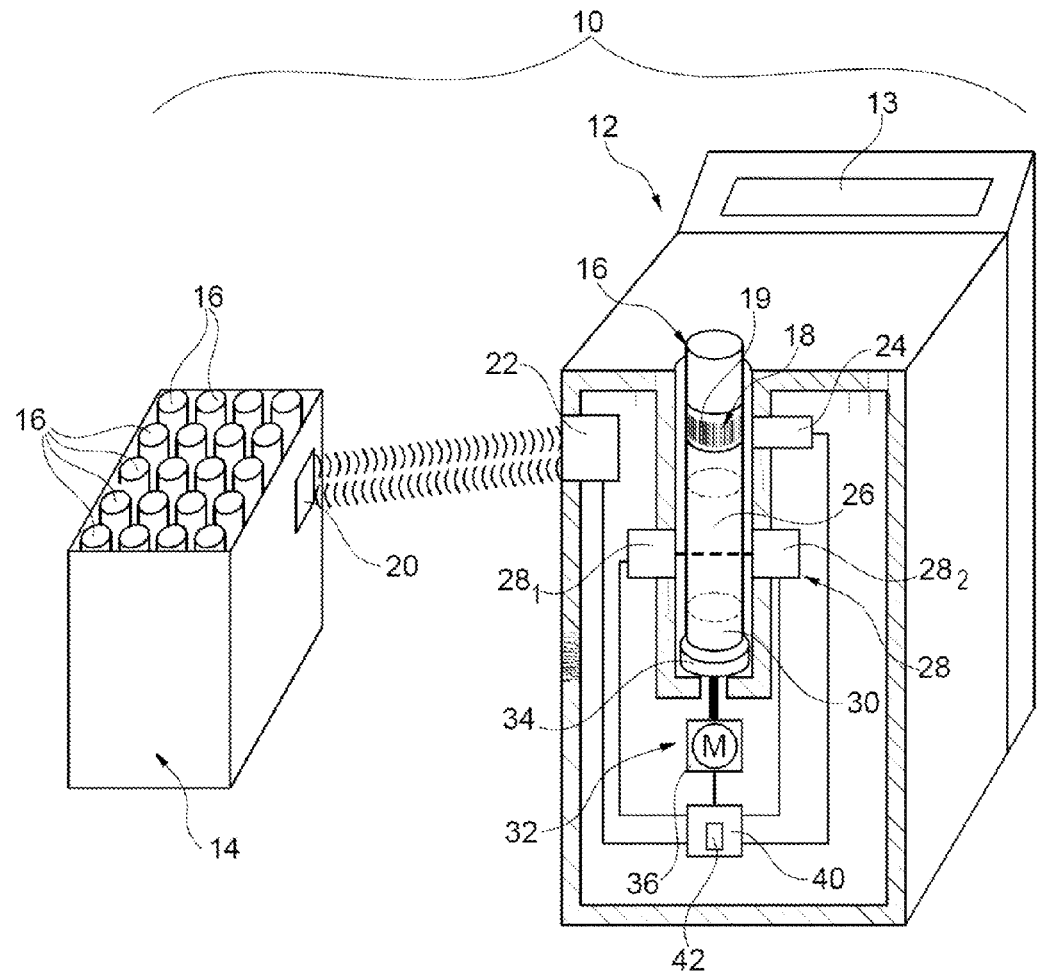
FIG. 1 shows a liquid analysis system including a test cuvette package with test cuvettes and an RFID parameter transponder, and an analyzer with a test cuvette placed therein.

In an embodiment, the liquid analysis system of the present invention comprises an analyzer with an RFID parameter reading device and an identifier reading device. The cuvette package is provided with an RFID parameter transponder, wherein the RFID parameter transponder comprises a batch identification memory holding a batch identification and a parameter memory holding batch-specific reagent data. An RFID reading device and an RFID transponder are electronic digital devices that communicate wirelessly via radio signals and thereby exchange data. An RFID transponder may be a passive or an active transponder. The batch identification memory and the parameter memory could physically be the same memory.

The cuvette package holds a plurality of test cuvettes of a batch, which test cuvettes each contain the same reagent that reacts in a color-changing manner with the analyte to be determined. In the present context, a batch refers to a batch both in a narrower or broader meaning, i.e., a product or production series that is homogeneous with respect to at least one of its reagents. In the present context, reagent data refer in particular, but not exclusively, to batch-specific calibration data, production data, quality assurance data and/or shelf-life data.

Each test cuvette has a batch-specific identifier including a batch identification that can be read by the identifier reading device.

A test cuvette placed in the analyzer is identified by the batch-specific identifier with the batch identification on the test cuvette being read by the identifier reading device of the analyzer. The identifier may be restricted to a rather small amount of information, as is inevitable, for example, with one or two dimensional bar codes. The amount of information that can be stored in a bar code is too small to store batch-specific reagent data. The batch-specific identification yields both the assignment of a test cuvette to a certain batch and the type of cuvette test, i.e., the analyte to be determined or the reagent contained in the test cuvette for that purpose.

The batch-specific reagent data are stored in the RFID parameter transponder of the cuvette package, which is addressed and read out by the RFID parameter reading device of the analyzer. In this manner, the batch identification from the batch identification memory and the associated batch-specific reagent data from the parameter memory of the RFID parameter transponder are transferred to corresponding memories of the analyzer. This can occur, for example, every time a new cuvette package is opened for the first time, or every time a test cuvette having a batch identification unknown to the analyzer is placed in the analyzer for the first time and the analyzer has signaled this fact optically and/or acoustically. The batch-specific reagent data no longer have to be entered manually into the analyzer.

In this way, calibration data, shelf-life data, production data and/or quality assurance data etc. can be transmitted as the batch-specific reagent data. Since an RFID transponder can store very large amounts of information, the analyzer can thus be provided with all information required for an exact, reliable and comprehensively documented determination of an analyte. The magnitude of the information amount has no negative influence on the handling of the analysis system.

Since the batch-specific reagent data are no longer entered manually into the analyzer, but are transmitted automatically to the analyzer, an erroneous entry or input of reagent data is virtually excluded.

For a complete cuvette package filled with test cuvettes, only a single RFID parameter transponder is required. The additional costs of this measure are thus limited. Due to the fact that the RFID parameter transponder is provided on the cuvette package, but not on the test cuvette itself, the RFID transponder is inherently not exposed to chemicals, humidity and heating in an oven, which cannot be excluded with an RFID transponder affixed to a test cuvette. If the cuvette package is a multi-use package, the RFID parameter transponder can also be used several times by repeated re-programming.

The RFID parameter transponder may already be programmed during the production of the cuvette tests, i.e., during the filling of the test cuvettes with the reagent. The test cuvettes are provided with a batch-specific identifier having a batch identification, which corresponds to the batch identification written into the batch identification memory of the RFID parameter transponder. The batch-specific reagent data are stored in the parameter memory of the RFID parameter transponder of the cuvette package and, in doing so, are assigned to the corresponding batch identification. The test cuvettes packed in the associated cuvette package are provided with identifiers that contain the same batch identification.

For example, when the cuvette package is delivered or when the cuvette package is opened for the first time at the user's premises or when the first test cuvette of the cuvette package is used in a liquid sample analysis, the RFID parameter transponder of the cuvette package is read by the RFID parameter reading device of the analyzer, and the batch identification as well as the corresponding batch-specific calibration data are stored in the analyzer. The analyzer can, for example, store a plurality of batch-specific calibration data so that test cuvettes for different analytes and test cuvettes of different batches can be used anytime.

For an analysis, the water sample is introduced into the test cuvette and mixed with the reagent, the test cuvette is heated, if necessary, and is finally placed in the analyzer. The identifier reading device of the analyzer reads the identifier with the batch identification of the test cuvette and subsequently performs a photometric determination of the analyte in the liquid sample. The quantitative determination is done with the help of the batch-specific calibration data that are stored in the analyzer for the batch identifier read.

The identifier reading device and the RFID parameter reading device may be a single reading device which combines both functions. The batch-specific identifier may be a simple RFID transponder with a small memory capacity. The identifier reading device can, for example, be a reading device that is separate from the RFID reading device and has a different technical design. Both reading devices can thus be optimized for their tasks both technically and with a view to costs.

The identifier on the test cuvettes can, for example, be a bar code and the identifier reading device can, for example, be an optical bar code reading device. An example of a bar code is a so-called 2D bar code, i.e., a two-dimensional optical code that can represent a lot more information than a one-dimensional bar code. It is also possible to use color as a further dimension of the bar code.

The identifier can be provided anywhere on the test cuvette. Prior to being placed into the analyzer, the identifier of the test cuvette can be read by the identifier reading device. The bar code can, for example, be provided on the outer side of the test cuvette and the bar code reading device can, for example, be arranged in the analyzer such that the bar code can be read when the test cuvette is placed in the analyzer. It is thereby provided that the identifier actually belongs to the test cuvette set into the analyzer. Such an arrangement also allows for an automatic reading of the identifier by the reading device.

In an embodiment of the present invention, the analyzer can, for example, comprise a test cuvette turning device for turning the inserted test cuvette. The turning device turns the test cuvette set into the analyzer around the longitudinal axis of the test cuvette. This allows or facilitates finding and reading the test cuvette identifier by the identifier reading device of the analyzer. Turning the test cuvette during photometry also allows for a multi-spot measurement, whereby artifacts can be detected and excluded.

In an embodiment, the present invention also provides a method for operating an analyzer of a liquid analysis system which comprises the following method steps:

if a read-out instruction is present: reading the batch identification and the batch-specific reagent data from the RFID parameter transponder and storing these data in a reagent data memory, prior to each determination of an analyte: reading the batch-specific identifier of the test cuvette by means of the identifier reading device, and performing a quantitative photometric determination of the analyte in the liquid sample of the test cuvette using the associated reagent data.

The read-out instruction is either entered manually into the analyzer by the user, or it is triggered automatically as soon as an unknown batch identification is read by the identifier reading device, or the RFID parameter transponder enters the range of the RFID parameter reading device. If a read-out instruction is present, the batch-specific reagent data are read from the RFID parameter transponder into the reagent data memory of the analyzer.

Prior to every determination of an analyte, the batch-specific identifier of the test cuvette is read by the identifier reading device and the subsequent photometric quantitative determination of the analyte in the liquid sample is performed using the batch-specific reagent data stored in the reagent data memory of the analyzer.

FIG. 1 illustrates a liquid analysis system 10 for the photometric determination of an analyte in a liquid sample. The system is a so-called laboratory analysis system as it is typically used to determine an analyte in a liquid at defined moments. The analysis system 10 is thus suited for a coarse-meshed manual monitoring of an analyte or for quality control, but it is not suited as an automatic transducer for process control purposes. The analysis system 10 comprises an analyzer 12 with a photometer 28 and a cuvette package 14 holding a plurality of test cuvettes 16.

Figure 2:
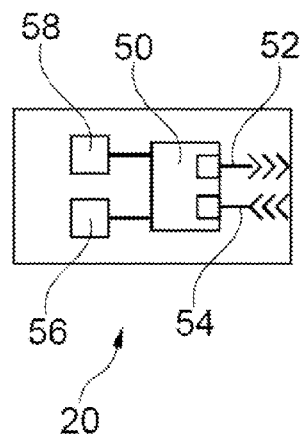
FIG. 2 shows a schematic illustration of the RFID parameter transponder in FIG. 1.

A test cuvette 16 is formed by a rather small test tube that is circular in cross section and is made of transparent glass or plastic material, the tube being filled with a reagent 30 which reacts with the analyte to determine by a change of color. The cuvette package 14 exclusively holds test cuvettes 16 of a single batch. All test cuvettes 16 of a single batch have identical reagent data. The cuvette package 14 comprises an RFID parameter transponder 20 illustrated schematically and in detail in FIG. 2.

The active RFID parameter transponder 20 comprises a control unit 50, a transmitter antenna 52, a receiver antenna 54, a batch identification memory 56 and a parameter memory 58. The batch identification memory 56 holds a unique and distinctive identifier that is identical with the batch-specific identifiers 18 provided on the test cuvettes 16. The parameter memory 58 holds the corresponding batch-specific reagent data, for example, calibration data, an expiry date, as well as further production and quality assurance data.

As the identifier 18 holding the batch identification, the test cuvettes 16 each have a so-called two-dimensional 2D-bar code 19 on their outside.

The analyzer 12 comprises a display 13 to display information, such as operating instructions and error reports, for example, and in particular to display the quantitative result of an analyte determination.

The analyzer 12 is controlled by a control unit 40 including a reagent data memory 42. The analyzer 12 comprises a photometer 28 substantially formed by a photometer transmitter 28$_1$ and a photometer receiver 28$_2$.

The analyzer 12 comprises an identifier reading device 24 designed as a vertically reading line camera or as an area camera and adapted to read the two-dimensional bar code 19 of an inserted test cuvette 16 if the test cuvette 16 is turned into a corresponding position, or, in the case of an area camera, is turned even during reading.

The analyzer 12 comprises a turning device 32 formed by a rotary motor 36 and a turntable 34. The test cuvette 16, inserted into a vertical cuvette shaft, stands on the turntable 34 and can be turned by means of the turning device 32. The turning device 32 turns the test cuvette 16 both to position the identifier 18, possibly also while the 2D bar code 19 is read by the identifier reading device 24, and during the photometry performed by the photometer 28 on the water sample 26.

Further, the analyzer 12 comprises an RFID parameter reading device 22 adapted to communicate with the RFID parameter transponder 20 of the cuvette package 14 such that the RFID parameter reading device 22 can read the batch identification and the associated batch-specific reagent data from the transponder 20. Reading may be started, for example, through a corresponding key input by the user at the analyzer 12. The read-out reagent data are stored in the reagent data memory 42.

For the determination of an analyte, first, a water sample is filled into a test cuvette 16 and the test cuvette 16 is set into the analyzer. Prior to the actual determination of an analyte, the batch-specific identifier or the batch identification of the test cuvette 16 stored therein is read by the identifier reading device 24. If the reagent data memory 42 already holds reagent data for this batch identification, the photometric quantitative determination of the analyte in the liquid sample is then performed by the photometer 28 and with the use of the batch-specific reagent data stored in the reagent data memory 42 of the analyzer 12.

If the batch identification is unknown to the analyzer 12, the user is requested prior to the photometry operation to read the reagent data from the RFID parameter transponder 20 of the respective cuvette package 14. The photometry is then performed.

The present invention is not limited to embodiments described herein; reference should be had to the appended claims.

What is claimed is:

1. A method of using an analyzer for a liquid analysis system, the method consisting of:
   providing an analyzer comprising,
      a photometer,
      an RFID parameter reading device,
      a 2D bar code reading device, and
      a reagent data memory,
      the 2D bar code reading device being provided separately from the RFID parameter reading device;
   providing a liquid analysis system comprising:
      the analyzer, and
      a cuvette package comprising
         an RFID parameter transponder which stores a batch identification and batch-specific reagent data, the RFID parameter transponder being configured to provide a read-out instruction, and
         a plurality of test cuvettes of one batch, each test cuvette comprising a reagent and a 2D bar code comprising the batch identification, the 2D bar code being configured to be read by the 2D bar code reading device;
   reading the batch identification and batch-specific reagent data from the RFID parameter transponder, if the read-out instruction is present;
   storing the batch identification and batch-specific reagent data in the reagent data memory, if the read-out instruction is present;
   reading the 2D bar code of the test cuvette with the 2D bar code reading device of the analyzer prior to a determination of an analyte;
   assigning the test cuvette to the cuvette package and to the batch-specific reagent data; and
   using the analyzer to perform a quantitative photometric determination of the analyte in a liquid sample of the test cuvette using batch-specific reagent data.

2. A method of using a cuvette package with a plurality test cuvettes in a liquid analysis system, the method consisting of:
   providing a cuvette package comprising:
      an RFID parameter transponder configured to provide a read-out instruction and to store a batch identification and batch-specific reagent data, and
      a plurality of test cuvettes of one batch, each test cuvette comprising a reagent and a 2D bar code comprising the batch identification, the batch identification being configured to be read by a 2D bar code reading device;
   providing a liquid analysis system comprising,
      an analyzer comprising,
         a photometer,
         an RFID parameter reading device,
         the 2D bar code reading device, and
         a reagent data memory,
         the 2D bar code reading device being provided separately from the RFID parameter reading device, and
      the cuvette package;
   reading the batch identification and batch-specific reagent data from the RFID parameter transponder, if the read-out instruction is present;
   storing the batch identification and batch-specific reagent data in the reagent data memory, if the read-out instruction is present;
   reading the 2D bar code of the test cuvette with the 2D bar code reading device prior to a determination of an analyte;
   assigning the test cuvette to the cuvette package and to the batch-specific reagent data; and
   performing a quantitative photometric determination of the analyte in a liquid sample of the test cuvette using the batch-specific reagent data.

* * * * *